United States Patent
Wikfors et al.

(10) Patent No.: US 9,945,762 B2
(45) Date of Patent: Apr. 17, 2018

(54) APPARATUS AND METHOD FOR INTRODUCING SAMPLE INTO A SEPARATION UNIT OF A CHROMATOGRAPHY SYSTEM WITHOUT DISRUPTING A MOBILE PHASE

(71) Applicant: AGILENT TECHNOLOGIES, INC., Loveland, CO (US)

(72) Inventors: Edwin E. Wikfors, Landenberg, PA (US); Brian A. Bidlingmeyer, Frazer, PA (US); Klaus Witt, Keltern (DE)

(73) Assignee: Agilent Technologies, Inc., Santa Clara, CA (US)

( * ) Notice: Subject to any disclaimer, the term of this patent is extended or adjusted under 35 U.S.C. 154(b) by 47 days.

(21) Appl. No.: 14/586,882

(22) Filed: Dec. 30, 2014

(65) Prior Publication Data

US 2016/0187304 A1  Jun. 30, 2016

(51) Int. Cl.
| | |
|---|---|
| G01N 30/06 | (2006.01) |
| G01N 1/28 | (2006.01) |
| G01N 30/20 | (2006.01) |
| G01N 30/36 | (2006.01) |
| G01N 30/34 | (2006.01) |

(52) U.S. Cl.
CPC ............... *G01N 1/28* (2013.01); *G01N 30/20* (2013.01); *G01N 30/36* (2013.01); *G01N 2030/202* (2013.01); *G01N 2030/207* (2013.01); *G01N 2030/342* (2013.01)

(58) Field of Classification Search
CPC ............................ G01N 30/00; G01N 2030/00
USPC ..................................................... 210/198.1
See application file for complete search history.

(56) References Cited

U.S. PATENT DOCUMENTS

| | | | | | |
|---|---|---|---|---|---|
| 4,158,630 | A | * | 6/1979 | Stearns | G01N 30/20 210/198.2 |
| 4,300,393 | A | * | 11/1981 | Stearns | G01N 30/20 73/863.11 |
| 4,984,602 | A | * | 1/1991 | Saito | G05D 16/2013 137/487.5 |
| 5,411,707 | A | * | 5/1995 | Hiatt | B01D 3/10 422/68.1 |

(Continued)

FOREIGN PATENT DOCUMENTS

| | | |
|---|---|---|
| JP | 2010101875 A | 5/2010 |
| WO | 2013134222 A1 | 9/2013 |

OTHER PUBLICATIONS

English Translation of JP2010101875.

*Primary Examiner* — Harshad R Patel
*Assistant Examiner* — Tran M Tran

(57) ABSTRACT

A method and a system for introducing a sample into a mobile phase of a chromatography system is provided. The method includes initially directing the mobile phase directly into a separation unit of the chromatography system, bypassing a sample loop, the mobile phase including a combined solvent, metered from a pressurized first solvent and a second solvent; loading the sample into the sample loop, while the mobile phase continues to be directed directly into the separation unit; pressurizing the sample in the sample loop with the pressurized first solvent, while the mobile phase continues to be directed directly into the separation unit; and switching the sample loop into the mobile phase, thereby introducing the pressurized sample to the separation unit.

11 Claims, 8 Drawing Sheets

(56) References Cited

U.S. PATENT DOCUMENTS

| | | | | |
|---|---|---|---|---|
| 5,714,676 A * | 2/1998 | Hase | ............... | G01N 30/06 73/23.41 |
| 6,012,488 A * | 1/2000 | Nichols | ............... | F16K 11/0743 137/625.11 |
| 6,382,035 B1 * | 5/2002 | Nichols | ............... | G01N 30/20 73/863.72 |
| 6,576,125 B2 * | 6/2003 | Berger | ............... | B01D 15/14 210/198.2 |
| 6,610,201 B2 * | 8/2003 | Dourdeville | ............... | B01D 15/166 210/101 |
| 6,648,609 B2 * | 11/2003 | Berger | ............... | 137/512 |
| 6,730,228 B2 * | 5/2004 | Petro | ............... | B01D 15/1878 210/143 |
| 7,574,901 B2 * | 8/2009 | Iwata | ............... | G01N 30/20 137/625.46 |
| 7,797,988 B2 * | 9/2010 | Schultz | ............... | G01N 30/80 73/61.55 |
| 7,927,477 B2 * | 4/2011 | Paul | ............... | B01D 61/56 204/600 |
| 8,297,107 B2 * | 10/2012 | Tipler | ............... | G01N 30/32 73/23.42 |
| 8,312,762 B2 * | 11/2012 | Fadgen | ............... | G01N 30/20 73/61.55 |
| 8,567,441 B2 * | 10/2013 | Maeda | ............... | F16K 11/074 137/240 |
| 8,621,915 B2 * | 1/2014 | Liu | ............... | G01N 30/463 210/656 |
| 8,685,218 B2 * | 4/2014 | Paul | ............... | B01D 61/56 204/600 |
| 8,716,025 B2 * | 5/2014 | Witt | ............... | G01N 30/463 204/451 |
| 8,770,046 B2 * | 7/2014 | Maeda | ............... | G01N 30/20 73/863.01 |
| 8,944,102 B1 * | 2/2015 | Wiederin | ............... | F16K 11/0743 137/625.46 |
| 9,115,815 B2 * | 8/2015 | Gerhardt | ............... | F16K 11/0743 |
| 9,194,504 B2 * | 11/2015 | Cormier | ............... | F16K 11/0655 |
| 9,228,982 B2 * | 1/2016 | Ebsen | ............... | G01N 30/20 |
| 9,239,319 B2 * | 1/2016 | Sims | ............... | G01N 30/463 |
| 9,347,919 B2 * | 5/2016 | Fukumoto | ............... | G01N 30/06 |
| 9,618,128 B2 * | 4/2017 | Dourdeville | ............... | G01N 30/20 |
| 2002/0146349 A1 * | 10/2002 | Gygi | ............... | G01N 30/08 422/70 |
| 2005/0214130 A1 * | 9/2005 | Yang | ............... | F04B 7/0076 417/26 |
| 2007/0199874 A1 * | 8/2007 | Ito | ............... | G01N 30/463 210/198.2 |
| 2012/0285558 A1 * | 11/2012 | Witt | ............... | F04B 13/00 137/544 |
| 2013/0008859 A1 * | 1/2013 | Witt | ............... | G01N 30/463 210/767 |
| 2013/0134095 A1 * | 5/2013 | Anderer | ............... | B01D 15/1878 210/656 |
| 2013/0180404 A1 * | 7/2013 | Fogelman | ............... | B01D 19/0057 95/266 |
| 2015/0047422 A1 * | 2/2015 | Berg | ............... | B01D 15/14 73/61.56 |
| 2015/0059451 A1 * | 3/2015 | Witt | ............... | B01L 3/502784 73/61.55 |
| 2015/0122655 A1 * | 5/2015 | Choikhet | ............... | G01N 30/463 204/601 |

\* cited by examiner

APPARATUS AND METHOD FOR INTRODUCING SAMPLE INTO A SEPARATION UNIT OF A CHROMATOGRAPHY SYSTEM WITHOUT DISRUPTING A MOBILE PHASE

BACKGROUND

Generally, chromatography systems separate analytes of a sample using a separation unit, such as a chromatographic column. For example, a sample containing various analytes, such as chemical compounds, or other sample constituents, dissolved in a solvent solution may be injected into a mobile phase fluid stream with an injection valve, where the mobile phase typically comprises one or more solvents. The sample-containing mobile phase flows through the chromatographic column which selectively retains the analytes from the sample. The analytes from the sample experience a differential retention with the column's stationary phase, e.g., using packing material or sorbent within the chromatographic column, and the relative elution strength of the mobile phase. The separated analytes may then be directed to a detector for detection and analysis, where each of the analytes emerges from the chromatographic column at a different time corresponding to the respective differential retention of that analyte within the chromatographic column. Detection over time results in "peaks" respectively corresponding to the analytes of the sample, where the magnitude of each peak correlates to the amount of the corresponding analytes in the sample. In preparative chromatography systems, the separated sample constituents may be collected by various fraction collection devices.

Typically, the mobile phase is a mixture of solvents provided by corresponding pumping systems. The solvents include at least a strong solvent and a weak solvent referring to the solvents relative elution strength in relation to each other and to the stationary phase being used. The strong solvent favors a partitioning of the sample components into the mobile phase, thus lessening retention, or providing faster transiting of the chromatographic column. The weak solvent favors partitioning of the sample components on the column's stationary phase thus increasing retention, and may serve to moderate the effects of the strong solvent. Attempts are made to balance the mobile phase composition or ratio between the strong and weak solvents in order to provide an acceptable compromise between speed of the chromatography operation and quality of the analytical results.

One type of chromatography system is supercritical fluid chromatography (SFC). SFC with packed columns typically uses an organic solvent, such as methanol, as the strong solvent and highly compressed dense carbon dioxide ($CO_2$) as the weak solvent.

Conventional chromatography systems disrupt the mobile phase to the chromatographic column in order to pressurize the sample loop and/or introduce the sample loop into the mobile phase, including interrupting flow of the mobile phase to the chromatographic column. That is, the mobile phase flow is essentially disconnected from the column, while the sample loop is pressurized with the mobile phase from a pump outlet before the mobile phase flow is essentially rejoined to the column to again perform the chromatography. The switching of an unpressurized element into the flow stream stops the flow of the mobile phase to the column for the period of time required to pump the mobile phase at or near the volume of the sample loop, and to pressurize the same. Although the interruption of mobile phase flow may be relatively short in duration for small volume sample loops (e.g., less than about 10 μl) typically used in analytical SFC, it is still undesirable. Further, for large volume partially filled sample loops (e.g. volumes greater than 20 μl), or very large volumes associated with solid phase extraction (SPE) cartridges or other types of pre-columns (e.g., greater than about 250 μl), the interruption is significant, sometimes lasting for more than 7 seconds, for example, and causing pressure impulse perturbations greater than 50 bar. During this period, the mobile phase pumping system, and thus the mobile phase at the head of the column, loses pressurization.

In addition to interruption of the flow of mobile phase or other fluid components to the chromatographic column while the sample loop is being pressurized, disruption of the mobile phase may further include the mobile phase within the column flowing backwards from the column into the sample loop if the sample loop is not isolated during the pressurization. The insertion of an unpressurized volume into the flow stream feeding the column can cause a negative pressure gradient between the unpressurized sample loop and the highly pressurized head of the column. This negative pressure gradient causes a disruption where the mobile phase can flow out of the head of the column to fill the void created by the unpressurized loop. A backwards flow within the head of the column is considered poor practice as it can lead to failures in the column's packing.

It is therefore desirable to inject sample into a loop, to pressurize the sample loop and to introduce the pressurized sample loop into the mobile phase without disrupting the mobile phase, such as interrupting flow of the mobile phase into the column.

BRIEF DESCRIPTION OF THE DRAWINGS

The representative embodiments are best understood from the following detailed description when read with the accompanying drawing figures. Wherever applicable and practical, like reference numerals refer to like elements.

DETAILED DESCRIPTION

Figure 1:
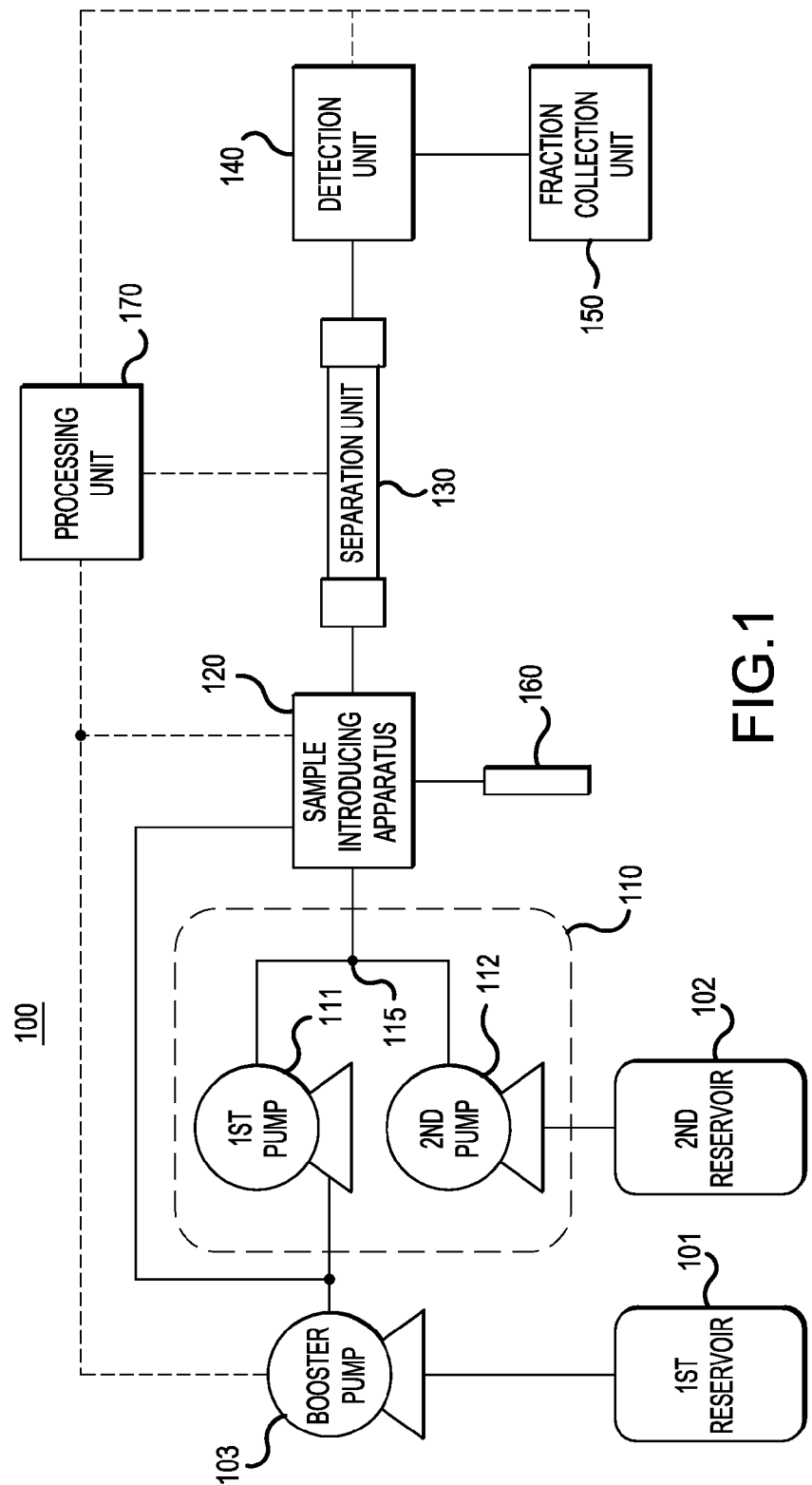
FIG. 1 is a simplified block diagram of a chromatography system, according to a representative embodiment.

In the following detailed description, for purposes of explanation and not limitation, illustrative embodiments disclosing specific details are set forth in order to provide a thorough understanding of embodiments according to the present teachings. However, it will be apparent to one having had the benefit of the present disclosure that other embodiments according to the present teachings that depart from the specific details disclosed herein remain within the scope of the appended claims. Moreover, descriptions of well-known devices and methods may be omitted so as not to obscure the description of the example embodiments. Such methods and devices are within the scope of the present teachings.

Generally, it is understood that as used in the specification and appended claims, the terms "a", "an" and "the" include both singular and plural referents, unless the context clearly dictates otherwise. Thus, for example, "a device" includes one device and plural devices.

As used in the specification and appended claims, and in addition to their ordinary meanings, the terms "substantial" or "substantially" mean to within acceptable limits or degree. For example, "substantially cancelled" means that one skilled in the art would consider the cancellation to be acceptable. As a further example, "substantially removed" means that one skilled in the art would consider the removal to be acceptable.

As used in the specification and the appended claims and in addition to its ordinary meaning, the term "approximately" means to within an acceptable limit or amount to one having ordinary skill in the art. For example, "approximately the same" means that one of ordinary skill in the art would consider the items being compared to be the same.

Generally, in a chromatography system, a mobile phase delivery (pumping) system has the simultaneous duties of compression and the metering for delivery of mobile phase to a chromatographic column. A split in responsibility can be manifested in a pumping system physically compressing or boosting with one pump and metering the fluid with a second pump subsequent to the first pump. A valve assembly may be used to block the end of a sample loop or retentive cartridge, such as an SPE cartridge, containing a sample, while connecting the other end to a fluidic junction located in between a pressure boosted mobile phase source and its metering pumping means. By connecting to a pressurized junction of suitable capacity, a mobile phase component may be used to pressurize the sample loop or SPE cartridge without decoupling the mobile phase delivery (metering) from the chromatographic column.

The pressurization of the sample loop or SPE cartridge may be performed without regard to loop size, exquisite or exotic valve positioning mechanisms for partial isolation, thus reducing both the cost and complexity of implementation. Further, very large capacity loops and cartridges may be implemented and switched in-stream without any of the previous perturbation effects. A subtle, yet beneficial aspect of utilizing the first (e.g., weak) solvent for pressurization of the sample loop is that decreasing the proportion of strong sample solvent within the sample loop reduces the relative total solvent strength during the initial sample application of sample analytes onto the column. This reduction in total solvent strength will result in favoring partitioning onto the stationary phase and thus improved focusing of sample analytes onto the column yielding sharper (narrower) peaks and improved resolution within the analytical results.

FIG. 1 is a simplified block diagram of a chromatography system, according to a representative embodiment.

Referring to FIG. 1, chromatography system 100 includes mobile phase pumping system 110, sample introducing apparatus 120, separation unit 130, detection unit 140 and (optionally) a fraction collection unit 150. The mobile phase pumping system 110 is configured to receive at least two fluids, referred to as first solvent and second solvent, from first reservoir 101 and second reservoir 102, respectively. Typically, the fluids received by the mobile phase pumping system 110 include a weak solvent and a strong solvent, which are mixed in various proportions to provide a combined solvent in a flowstream of the mobile phase, as discussed below. For example, in an SFC system, the first solvent provided by the first reservoir 101 is a weak solvent, such as carbon dioxide ($CO_2$) or nitrous oxide ($N_2O$), and the second solvent provided by the second reservoir 102 is a strong solvent, such as methanol or other organic solvent. In alternative configurations, the weak solvent may be a liquid, such as pentane, heptane or hexane, for example. In the depicted embodiment, the first solvent is pressurized (or compressed) by a booster pump 103 before being provided to the mobile phase pumping system 110. In an alternative embodiment (not shown), where the weak solvent is not a gas, but a less compressible liquid at ambient pressure, a portion of the first solvent may be directly provided to the mobile phase pumping system 110, that is, before pressurization by the booster pump 103, while the booster pump 103 provides a portion of the first solvent for pressurization usage.

The mobile phase pumping system 110 includes a first pump 111 for metering the (pressurized) first solvent and a second pump 112 for metering the second solvent. The metered portions of the first and second solvents are mixed at junction 115 to provide a combined solvent (flowing in a combined flow stream), which forms the chromatographic mobile phase. That is, the mobile phase pumping system 110 meters the combined solvent as the mobile phase to the separation unit 130, where the mobile phase is pressurized by pumping against head pressure of the separation unit 130. The junction 115 may be replaced by a mixer (not shown) without departing form the scope of the present teachings. In an embodiment, the first and second pumps 111 and 112 may be included in a single binary pump (indicated by dashed lines), although the first and second pumps 111 and 112 may include multiple piston, positive displacement pumps or other types of pumps capable of delivering a pulseless consistent flow stream, for example, without departing form the scope of the present teachings. The booster pump 103 is operated separately from the first and second pumps 111 and 112 in that its primary function is to pressurize the first solvent from the first reservoir 101 rather than to participate in the metering of respective proportions of the first and second solvents. The pressure output by booster pump 103 is typically limited or controlled to just below the outlet pressure of subsequent pumps, such as first pump 111, so as to reduce or eliminate effects of a compressible first solvent from the first pump 111.

The sample introducing apparatus 120 injects sample into the mobile phase received from the mobile phase pumping system 110 to provide a sample-containing mobile phase to the separation unit 130. As discussed in detail below with reference to FIGS. 2-7, the sample introducing apparatus 120 includes a controllable valve assembly comprising a plurality of valves, a sample loop, and means for controlling loading of sample into the sample loop. For example, the means for controlling loading of the sample into the sample loop may be an autosampler including a needle for insertion into a vial 160 containing the sample, a needle seat for interfacing the needle with the sample loop, and a metering device to control drawing sample from the vial 160 into the needle to enable loading of the sample loop with the sample or expelling the contents of the needle into the needle seat. In various embodiments, the sample loop may consist of a solid phase extraction (SPE) cartridge, in which case the means for controlling loading into the sample loop comprises an SPE interface configured to load the sample from the vial 160 and to remove at least some sample solvent of the sample from the SPE cartridge, leaving analytes of the sample in the SPE cartridge. The analytes may include chemical compounds, and other sample constituents, for example.

The separation unit 130 generally comprises a column containing a stationary phase, and is configured to separate analytes of the sample in the sample-containing solution. The separation unit 130 may be implemented as one or more chromatographic columns, for example. More particularly, as discussed above, the separation unit 130 separates the analytes from the sample-containing stream by differential retention of the analytes, e.g., using packing material or sorbent typically applied within the inner walls of the separation unit 130. The analytes are eluted from the separation unit 130 at different times corresponding to the respective differential retentions of compounds within the chromatographic column. A detection unit 140 is provided for detecting separated analytes of the sample fluid.

The chromatography system 100 may further include a processing unit 170 connected to one or more of the booster pump 103, the mobile phase pumping system 110, the sample introducing apparatus 120, the separation unit 130, the detection unit 140, and the fraction collection unit 150 for controlling aspects of the chromatography process (control signal connections being indicated by dashed lines). It is understood that the various connections between the processing unit 170 and the other components of the chromatography system 100 may be any type of wired and/or wireless connections enabling control communications, without departing from the scope of the present teachings. For example, the processing unit 170 may control operation of pumps and pumping systems, pressure levels and/or mixture ratios in the sample introducing apparatus 120, as well as monitor various control parameters, such as flow rates, timing, and the like. The processing unit 170 may also control the amount of sample injected into the mixed solvent at the sample introducing apparatus 120. The processing unit 170 may further control the aspects of an SPE interface such as timing, valve positioning, sampling parameters, solvents and solvent flows when operating in conjunction with SPE cartridges. In addition, the processing unit 170 may receive data regarding sample detection (e.g., detected peaks, peak widths, resolution, efficiency, corresponding to analytes separated by the separation unit 130) from the detection unit 140. The received data may be displayed and/or stored for analysis, or used to adjust control elements relating to injection, pumping, or separation, for example.

Generally, the processing unit 170 may be implemented by a computer processor (e.g., of a personal computer (PC) or dedicated workstation), application specific integrated circuits (ASICs), field-programmable gate arrays (FPGAs), or combinations thereof, using software, firmware, hardwired logic circuits, or combinations thereof. A computer processor, in particular, may be constructed of any combination of hardware, firmware or software architectures, and may include memory (e.g., volatile and/or nonvolatile memory) for storing executable software/firmware executable code that allows it to perform the various functions. In an embodiment, the computer processor may comprise a central processing unit (CPU), for example, executing an operating system.

Figure 2A:
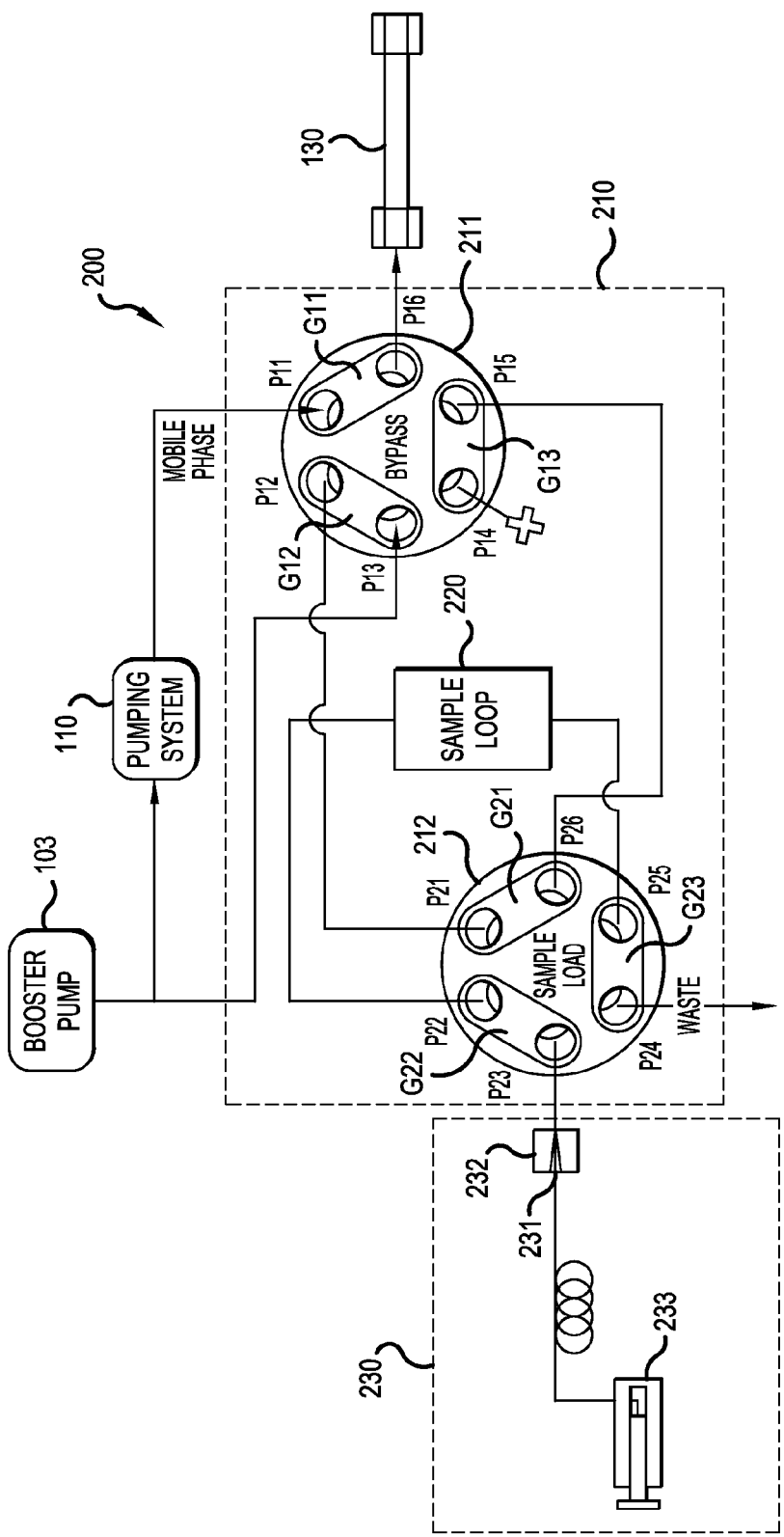
FIGS. 2A-2C are simplified block diagrams of a sample introducing apparatus in various configurations corresponding to steps for delivering pressurized sample via mobile phase to a separation unit, according to a representative embodiment.
Figure 2B:
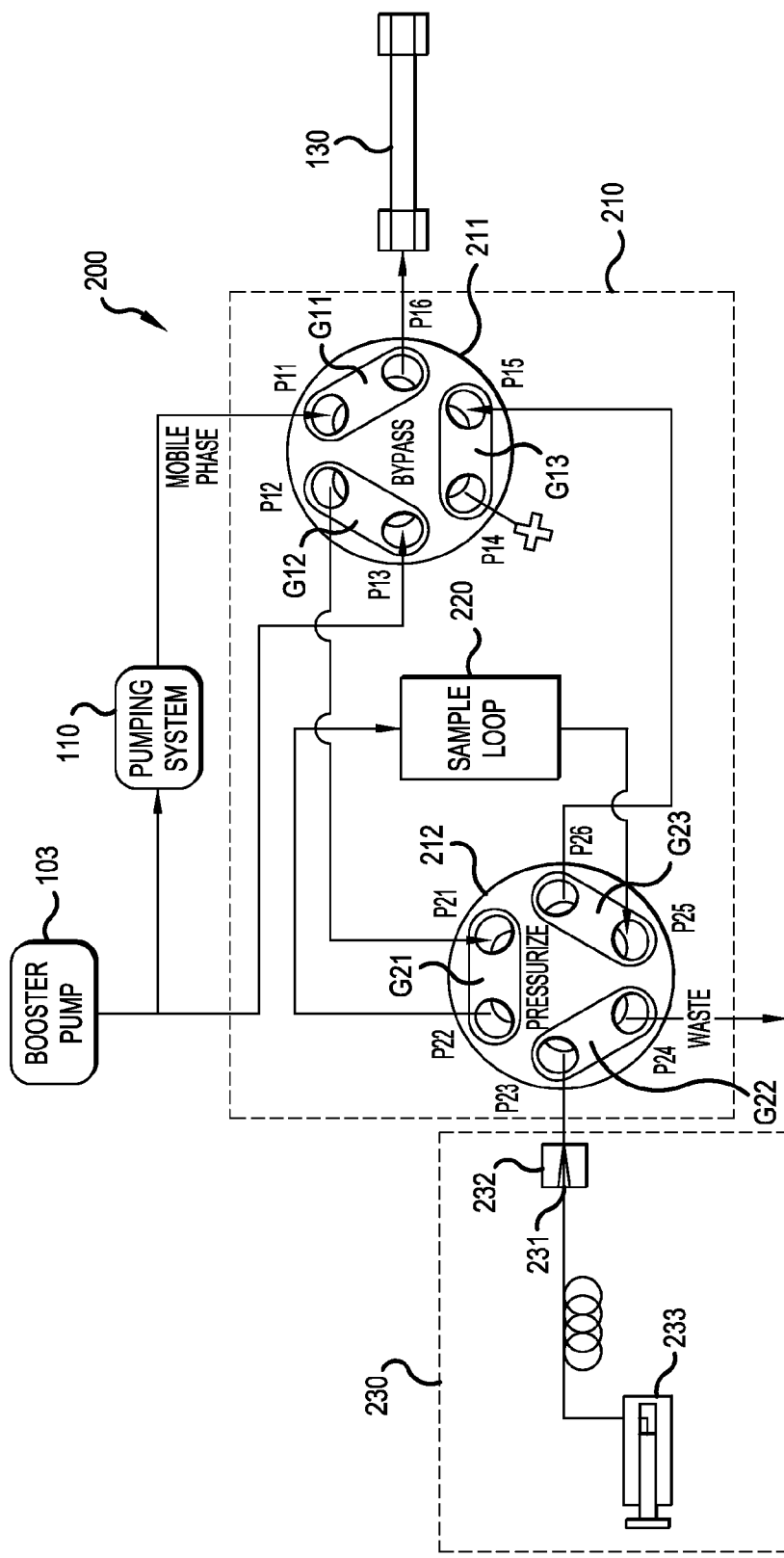
Figure 2C:
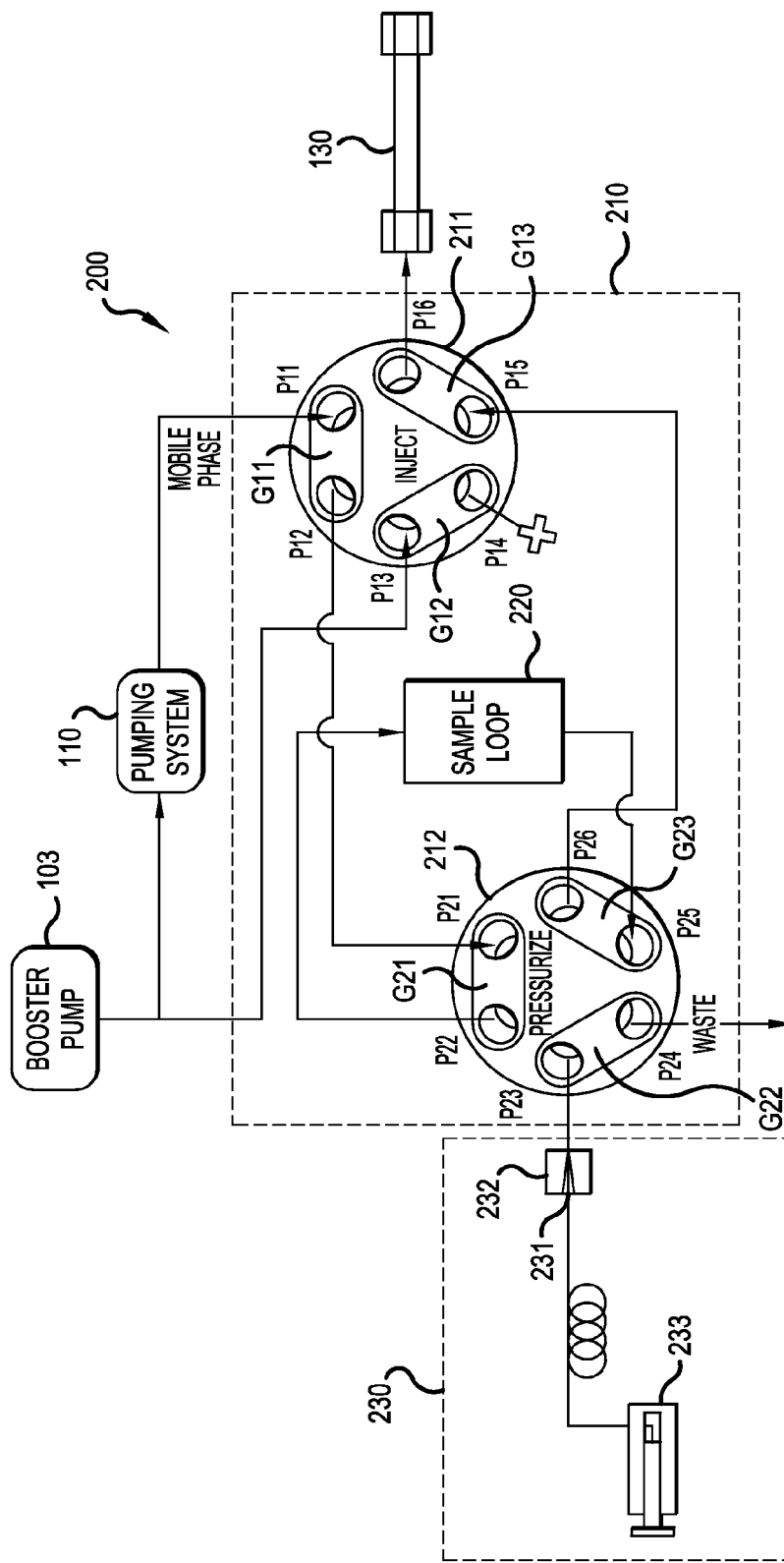

FIGS. 2A-2C are simplified block diagrams of a representative sample introducing apparatus in various configurations corresponding to steps for delivering pressurized sample via the mobile phase to a separation unit, according to a representative embodiment.

Referring to FIGS. 2A-2C, sample introducing apparatus 200 includes controllable valve assembly 210, a sample loop 220, and autosampler 230. FIGS. 2A-2C further show booster pump 103, mobile phase pumping system 110 and separation unit 130, discussed above with reference to FIG. 1, to indicate the context of the sample introducing apparatus 200 within a chromatography system (e.g., chromatography system 100). Generally, the sample loop 220 is pressurized and then switched into the mobile phase, thereby introducing pressurized sample to the separation unit 130, while the mobile phase from the mobile phase pumping system 110 remains pressurized and flow to the separation unit 130 is uninterrupted.

The controllable valve assembly 210 includes a first valve 211 and a second valve 212, both of which are multiple port valves capable of being switched (e.g., by rotation) to various configurations for accommodating different flow paths of the mobile phase and the sample. For example, in the depicted embodiment, both of the first and second valves 211 and 212 are two position, six port switching valves. The first valve 211 includes ports P11-P16 in a stator, and three channels or grooves G11-G13 in a rotor that is rotatable with respect to the stator. Each of the grooves G11-G13 may be arranged to selectively connect any two adjacent ports P11-P16, enabling fluid flow between the connected adjacent ports. Similarly, the second valve 212 includes six ports P21-P26 in a stator, and three channels or grooves G21-G23 in a rotor that is rotatable with respect to the stator. Each of the grooves G21-G23 may be arranged to selectively connect any two adjacent ports P1-P6, enabling fluid flow between the connected adjacent ports. Notably, the various embodiments allow use of standard rotor/groove spacing, that is, without requiring lengthened grooves on either the stator or rotor to provide connection. The sample introducing apparatus 200 may further include a check valve (not shown) on the line entering port P13 of the first valve 211. The check valve is arranged to receive the pressurized first solvent from the booster pump 103, while not allowing back flow into either the booster pump 103 or mobile phase pumping system 110, which could potentially contaminate or alter the mobile phase solvents.

As mentioned above, FIG. 2A depicts an initial configuration of the valve assembly 210 (first step) for delivering pressurized sample via the mobile phase to the separation unit 130. In particular, FIG. 2A shows a sample loading step in which the sample loop 220 is vented through waste and subsequently loaded, either partially or fully, via the autosampler 230 (e.g., via autosampler needle 231 and corresponding needle seat 232).

More particularly, the first valve 211 is configured (or switched) such that ports P11 and P16 are joined by groove G11, ports P12 and P13 are joined by groove G12, and ports P14 and P15 are joined by groove G13. In this configuration, the mobile phase (e.g., comprising combined weak and strong solvent) is received from the mobile phase pumping system 110 at port P11 and exits port P16 to the separation unit 130 of the chromatography system 100. In other words, the first valve 211 directs the mobile phase directly from the mobile phase pumping system 110 into the separation unit 130, bypassing the sample loop 220. Meanwhile, the pressurized first (e.g., weak) solvent is received from the booster pump 103 at port P13, exits port P12 of the first valve 211, is received at port P21 of the second valve 212, passes through groove G21 and exits port P26. The pressurized first solvent is then received at port P15 and exits port P14 of the first valve 211. Port P14 of the first valve 211 is plugged, causing the above-described path from P13 to P14 to fill with the pressurized first solvent at the pressure produced by the booster pump 103.

The second valve 212 is configured (or switched) such that ports P21 and P26 are joined by groove G21, ports P22 and P23 are joined by groove G22, and ports P24 and P25 are joined by groove G23. In this configuration, the mobile phase is received at port P21 from port P12 of the first valve 211, and returned from port P26 to port P15 of the first valve 211, as described above. The remaining ports are configured to load the sample loop 220 from the autosampler 230. That is, the metering device 233 draws the sample (comprising sample solvent and analytes) from a sample vial (e.g., vial 160) through the needle 231 and subsequently ejects the sample into the needle seat 232, thus pushing the extracted sample through the needle seat 232 into port P23 of the second valve 212. The sample exits from port P22 and enters the sample loop 220, loading the sample loop to a prescribed volume. If the sample loop 220 is filled, excess sample exits the sample loop 220, enters port P25 of the second valve 212, and exists port P25 to waste.

In an embodiment, the sample loop 220 may be implemented with a retentive cartridge, such as an SPE cartridge or pre-column. Such retentive cartridges typically have much larger volumes (e.g., greater than about 250 µl), as compared to a volume of traditional sample loops (e.g., between about 5 µl and about 10 µl). Due to the larger volume of an SPE cartridge, for example, sample is loaded into the sample loop 220 using an SPE interface (not shown), as which may utilize autosampler 230. The SPE interface loads sample onto the SPE cartridge with autosampler 230 in a manner described above. Multiple cycles of drawing the sample and ejecting into the SPE cartridge may be performed to fill or overfill the SPE cartridge as desired for a typical analysis. The SPE interface is further configured to subsequently remove at least some or most of the sample solvent of the sample from the SPE cartridge, while leaving sample analytes retained in the SPE cartridge. In an SFC system using an SPE interface, sample solvent removal may be performed by passing an inert gas, such as nitrogen (at an illustrative pressure of 250 psi) through the SPE cartridge. In such an embodiment, the nitrogen supply would alternately enter port P23 of the second valve 212 to provide the flow through the SPE cartridge. A selection valve (not shown) positioned immediately upstream of port P23 could readily alternate between an autosampler, a nitrogen flow, or even additional conditioning solvent flows in satisfying the requirements of the SPE interface. Notably, a retentive cartridge may be exchangeable, such that different retentive cartridges may be used for different solvents and/or different analyses.

FIG. 2B depicts a subsequent configuration of the valve assembly 210 (second step) for delivering pressurized sample via the mobile phase to the separation unit 130. In particular, FIG. 2B shows pressurization of the sample in the sample loop 220 with the pressurized first solvent, while the mobile phase continues to be directed directly into the separation unit 130.

More particularly, the first valve 211 remains in the same orientation or configuration, such that ports P11 and P16 are joined by groove G11, ports P12 and P13 are joined by groove G12, and ports P14 and P15 are joined by groove G13. In this configuration, the mobile phase continues to be provided directly to the separation unit 130 via port P11 and port P16 of the first valve 211. Also, the pressurized first solvent continues to be received from the booster pump 103 at port P13, and passed to the second valve 212 from port P12 of the first valve 211.

However, as shown in FIG. 2B, the second valve 212 is been configured (or switched) such that ports P21 and P22 are joined by groove G21, ports P23 and P24 are joined by groove G22, and ports P25 and P26 are joined by groove G23. In this configuration, the second valve 212 stops loading the sample into the sample loop 220, and the pressurized first solvent is received at port P21 from port P12 of the first valve 211, and provided to the sample loop 220 (or a retentive device, column, or SPE cartridge) via port P22, thereby pressurizing the sample in the sample loop 220. The output of the sample loop 220 (e.g., a mixture of the first solvent and the sample) is connected to port P25, which is connected to port P26 of the second valve 212. The output of port P26 is connected to port P15 of the first valve 211, which is connected to plugged port P24, as described above. Once the sample loop 220 is pressurized to the pressure provided by booster pump 103, there will not be any flow through the sample loop 220. Meanwhile, the sample provided by the autosampler 230 (or the corresponding interface, such as an SPE interface) is received by port P23, and exits port P24 of the second valve 212 to waste. In this manner, the mobile phase from the mobile phase pumping system 110 remains in direct communication with the separation unit 130, without interruption or other disturbance, while the sample loop 220 is being pressurized.

Notably, in above description, the second valve 212 was switched by rotating the rotor counter-clockwise with respect to the stator. However, this direction of movement is merely for purposes of illustration, and it is understood that the same practical configuration may be obtained by rotating the rotor of the second valve 212 clockwise with respect to the stator. In this case, ports P21 and P22 would be joined by groove G22, ports P23 and P24 would be joined by groove G23, and ports P25 and P26 would be joined by groove G21, without departing from the scope of the present teachings.

FIG. 2C depicts a subsequent configuration of the valve assembly 210 (third step) for delivering pressurized sample via the mobile phase to the separation unit 130. In particular, FIG. 2C shows placement of the sample loop 220 containing the pressurized sample into the mobile phase flow stream, thereby injecting the sample into the separation unit 130.

More particularly, the first valve 211 is configured (or switched) such that ports P11 and P12 are joined by groove G11, ports P13 and P14 are joined by groove G12, and ports P15 and P16 are joined by groove G13. In this configuration, the mobile phase entering the first valve 211 is diverted from through the second valve 212 in order to place the sample loop 220 containing the pressurized sample into the mobile phase, without interrupting flow of the mobile phase (still from port 16) into the separation unit 130. That is, the mobile phase is received from the mobile phase pumping system 110 at port P11 and exits port P12 to the port 21 of the second valve 212. The mobile phase exits port P22 and enters the sample loop 220, thereby placing the pressurized solvent into the combined solvent of the mobile phase. The output of the sample loop 220, now including the mobile phase containing the sample, enters port P25 and exits port P26, which is connected to port P15 of the first valve 211. The sample containing mobile phase enters port P15 and exits port P16, and is directed to the separation unit 130. Meanwhile, the sample provided by the autosampler 230 (or the SPE interface) continues to be received by port P23, and exits port P24 of the second valve 212 to waste. In this manner, the sample loop 220 is switched into the mobile phase, thereby introducing the pressurized sample to the separation unit 130.

Notably, in above description, the first valve 211 is switched by rotating the rotor counter-clockwise with respect to the stator. However, this direction of movement is merely for purposes of illustration, and it is understood that the same practical configuration may be obtained by rotating the rotor of the first valve 211 clockwise with respect to the stator. In this case, ports P11 and P12 would be joined by groove G12, ports P13 and P14 would be joined by groove G13, and ports P15 and P16 would be joined by groove G11, without departing from the scope of the present teachings.

Throughout the various steps and corresponding configurations of the valve assembly 210 discussed above with reference to FIGS. 2A-2C, the mobile phase from the mobile phase pumping system 110 remains pressurized while the sample loop 220 is being pressurized. Also, the pressurized sample is introduced into the mobile phase without interrupting delivery of the mobile phase to the separation unit 130. In other words, with all lines leading to and from the sample loop 220 being pressurized, flow of the mobile phase is not interrupted and diverted (temporarily) for pressurization, as in conventional chromatographic systems, thus avoiding mobile phase interruption or other disruption.

Figure 3A:
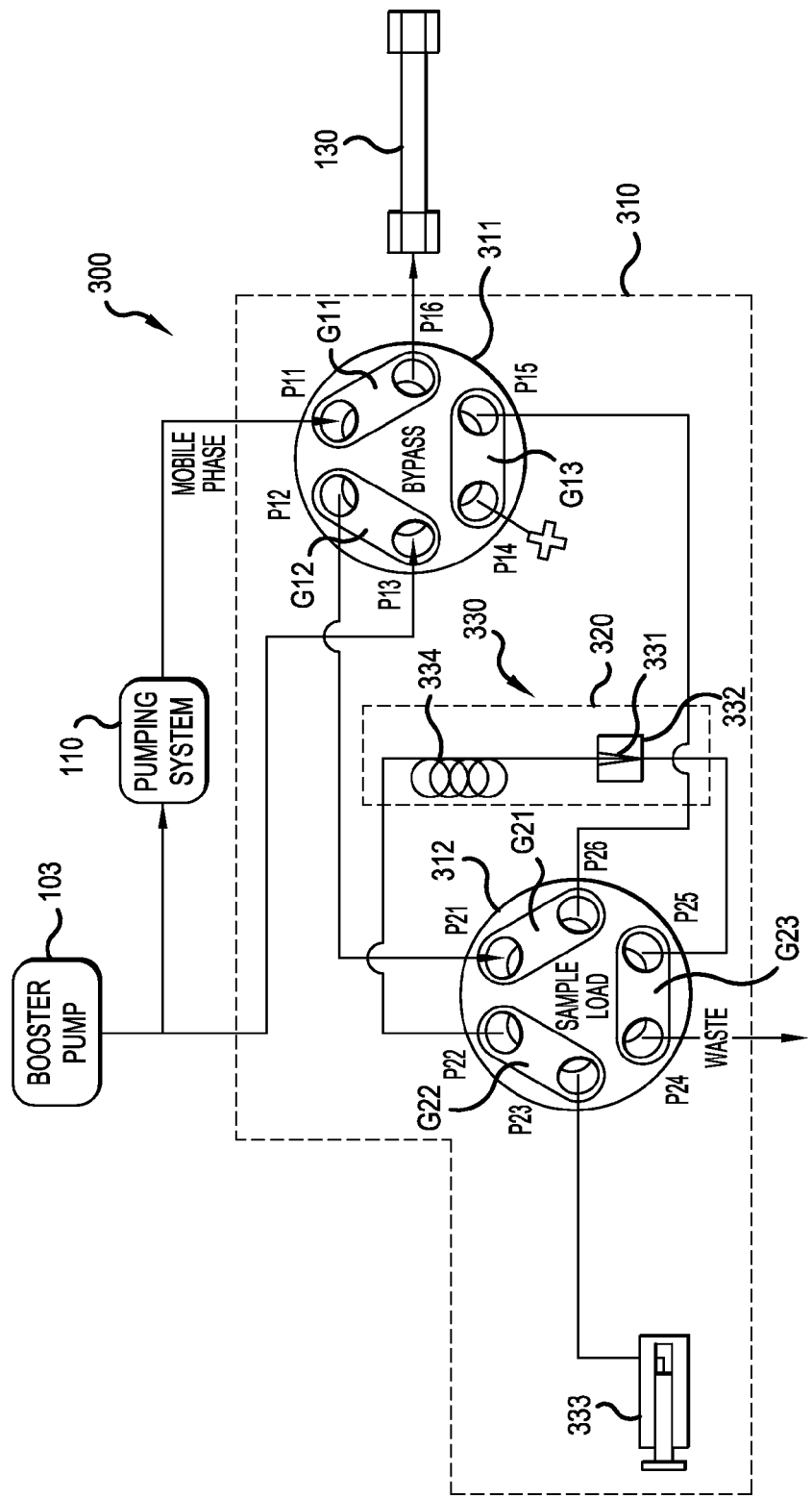
FIGS. 3A-3C are simplified block diagrams of a sample introducing apparatus in various configurations corresponding to steps for delivering pressurized sample via mobile phase to a separation unit, according to another representative embodiment.
Figure 3B:
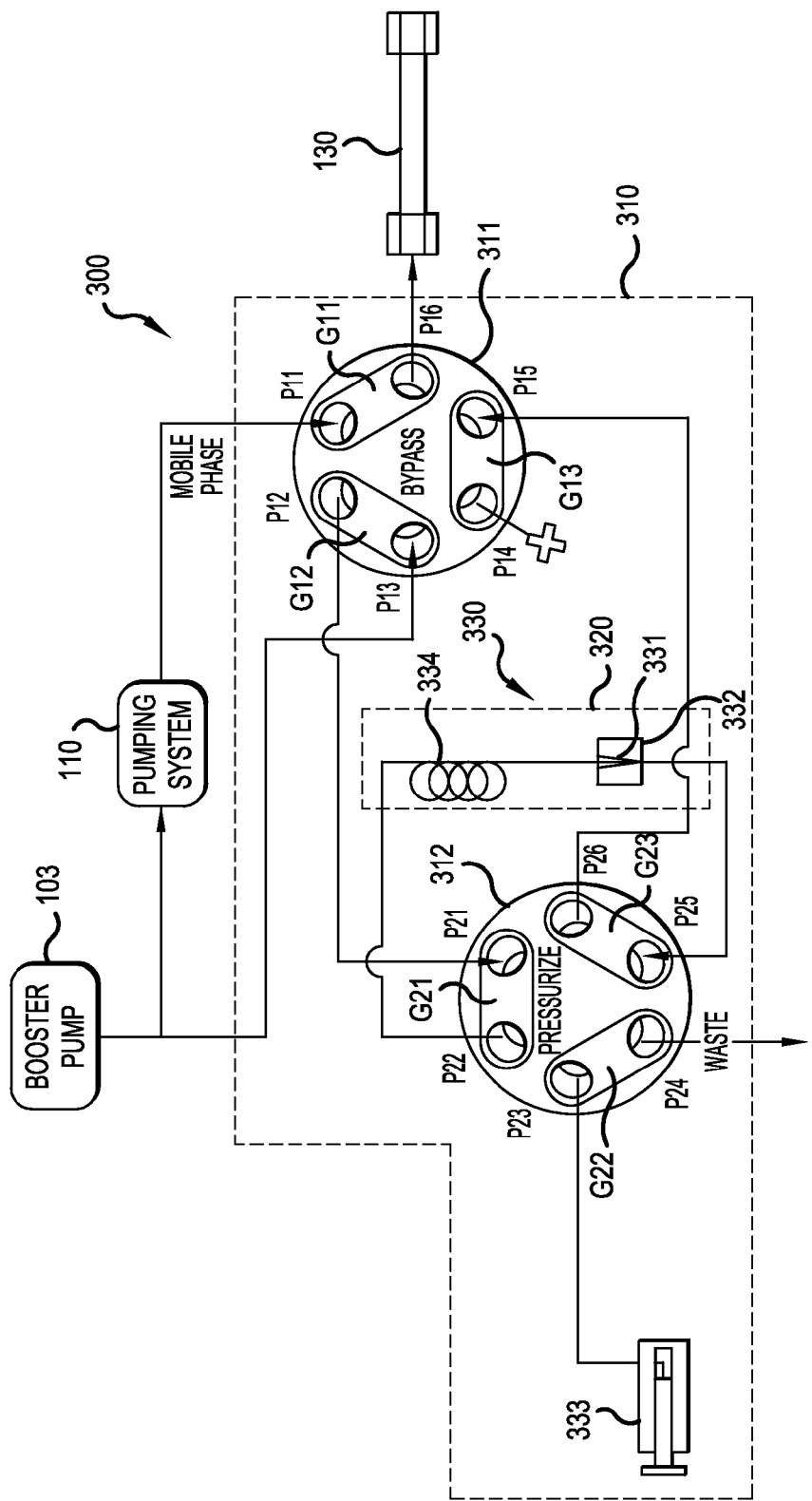
Figure 3C:
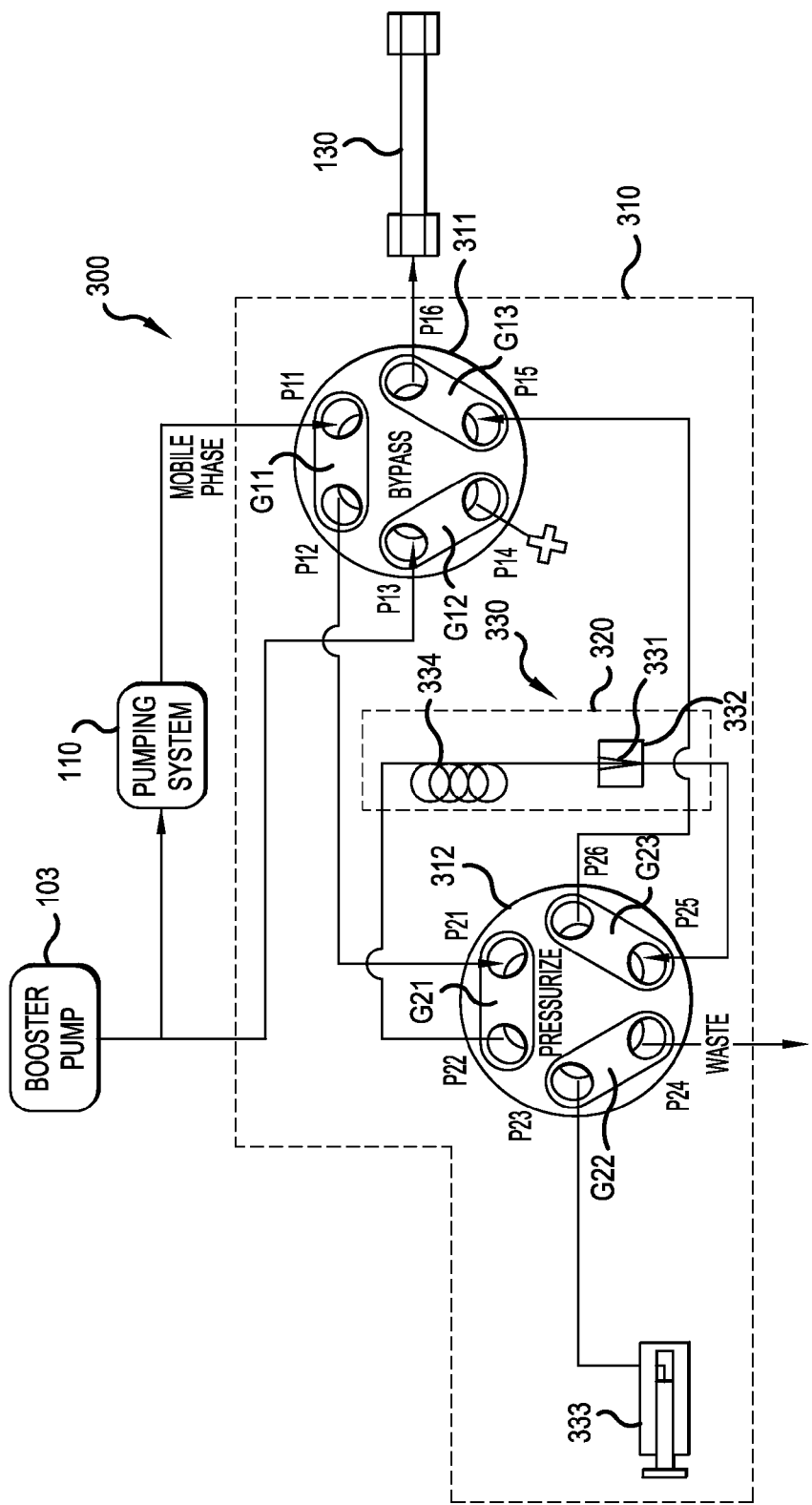

FIGS. 3A-3C are simplified block diagrams of a representative sample introducing apparatus in various configurations corresponding to steps for delivering pressurized sample via the mobile phase to a separation unit, according to another representative embodiment.

Referring to FIGS. 3A-3C, sample introducing apparatus 300 includes controllable valve assembly 310, a sample loop 320, and autosampler 330. The sample introducing apparatus 300 is intended for use with large volume "broken" sample loops (e.g., greater than about 100 µl), as compared to the normal sample loop 220 of FIGS. 2A-2C (e.g., when the sample loop 220 does not comprise a retentive cartridge). FIGS. 3A-3C further show booster pump 103, mobile phase pumping system 110 and separation unit 130, discussed above with reference to FIG. 1. Generally, according to the depicted embodiment, needle 331, needle capillary 334, and needle seat 332 of the autosampler 330 effectively become the sample loop 320, allowing for a very large volume needle capillary 334. With a very large volume needle capillary 334, large and/or variable amounts of sample can be drawn though the needle 331 and into needle capillary 334. Use of a very large sample loop (e.g. needle 331, needle capillary 334, and seat 332), partially filled, cannot be recommended for use without pressurization as the accompanying negative pressure gradient during injection would cause large perturbations and column back flow. The needle 331, needle capillary 334, and needle seat 332, acting as the sample loop is pressurized and then switched into the mobile phase, thereby introducing pressurized sample to the separation unit 130, while the mobile phase from the mobile phase pumping system 110 remains pressurized and flow of the mobile phase to the separation unit 130 is uninterrupted. Due to the larger volume of the sample loop 320, sample typically does not fill the sample loop 320, and thus any unfilled portion of the sample loop 320 is subsequently filled with the pressurized first solvent from the booster pump 103, as discussed below. The use of a weak solvent for pressurization, as opposed to mixtures at mobile phase composition, is beneficial in reducing the total solvent strength of the contents of the sample loop allowing larger volume injections while maintaining peak focusing than possible with conventional means.

The controllable valve assembly 310 includes a first valve 311 and a second valve 312, both of which are multiple port valves capable of being switched (e.g., by rotation) to various configurations for accommodating different flow paths of the mobile phase and the sample. For example, in the depicted embodiment, both of the first and second valves 311 and 312 are two position, six port switching valves. The first valve 311 includes ports P11-P16 in a stator, and three channels or grooves G11-G13 in a rotor that is rotatable with respect to the stator. Each of the grooves G11-G13 may be arranged to selectively connect any two adjacent ports P11-P16, enabling fluid flow between the connected adjacent ports. Similarly, the second valve 312 includes six ports P21-P26 in a stator, and three channels or grooves G21-G23 in a rotor that is rotatable with respect to the stator. Each of the grooves G21-G23 may be arranged to selectively connect any two adjacent ports P11-P16, enabling fluid flow between the connected adjacent ports. The sample introducing apparatus 300 may further include a check valve (not shown) on the line entering port P13 of the first valve 311, the check valve being arranged to receive the pressurized first solvent from the booster pump 103, while not allowing back flow into either booster pump 103 or mobile phase pumping system 110 which could potentially contaminate or alter the mobile phase solvents.

FIG. 3A depicts an initial configuration of the valve assembly 310 (first step) for delivering pressurized sample via the mobile phase to the separation unit 130. In particular, FIG. 3A shows a sample loading step in which the sample loop 320 is vented through waste and subsequently filled via the autosampler 330. As stated above, due to the large volume of the sample loop 320, it may be assumed that the autosampler needle 331, the needle seat 332, and the needle capillary 334 substantially provide the sample loop 320.

The first valve 311 is configured such that ports P11 and P16 are joined by groove G11, ports P12 and P13 are joined by groove G12, and ports P14 and P15 are joined by groove G13. In this configuration, the mobile phase (e.g., comprising combined weak and strong solvent) is received from the mobile phase pumping system 110 at port P11 and exits port P16 to the separation unit 130 of the chromatography system 100. In other words, the first valve 311 is configured to direct the mobile phase directly from the mobile phase pumping system 110 into the separation unit 130, bypassing the sample loop 320. Meanwhile, the pressurized first (e.g., weak) solvent is received from the booster pump 103 at port P13, exits port P12 of the first valve 311, is received at port P21 and exits port P26 of the second valve 312. The pressurized first solvent is then received at port P15 and exits port P14 of the first valve 311. Port P14 is plugged, causing the above-described path from P13 to P14 to fill with the pressurized first solvent at the pressure produced by the booster pump 103.

The second valve 312 is configured such that ports P21 and P26 are joined by groove G21, ports P22 and P23 are joined by groove G22, and ports P24 and P25 are joined by groove G23. In this configuration, the mobile phase is received at port P21 from port P12 of the first valve 311, and returned from port P26 to port P15 of the first valve 311, as described above. The remaining ports are configured to fill the sample loop 320/autosampler 330. That is, the metering device 333 of the autosampler 330 draws the sample (comprising sample solvent and analytes) from a sample vial (e.g., vial 160) through the needle 331 and into the needle capillary 334. In contrast to the embodiment of FIG. 2A, once the sample has been drawn into the needle capillary 334, the sample loading operation is complete as the metering device 333 is not required to push the sample into sample loop 320

FIG. 3B depicts a subsequent configuration of the valve assembly 310 (second step) for delivering pressurized sample via the mobile phase to the separation unit 130. In particular, FIG. 3B shows pressurization of the sample in the sample loop 320 with the pressurized first solvent, while the mobile phase continues to be directed directly into the separation unit 130 through the first valve 311.

More particularly, the first valve 311 remains in the same orientation or configuration, such that ports P11 and P16 are joined by groove G11, ports P12 and P13 are joined by groove G12, and ports P14 and P15 are joined by groove G13. In this configuration, the mobile phase continues to be provided directly to the separation unit 130 via port P11 and port P16 through groove G11 of the first valve 311. Also, the pressurized first solvent continues to be received from the booster pump 103 at port P13, and passed to the second valve 312 from port P12 of the first valve 311.

However, as shown in FIG. 3B, the second valve 312 is configured (or switched) such that ports P21 and P22 are joined by groove G21, ports P23 and P24 are joined by groove G22, and ports P25 and P26 are joined by groove G23. In this configuration, the pressurized first solvent is received at port P21 from port P12 of the first valve 311, and provided to the sample loop 320 (e.g., autosampler needle 331, needle capillary 334, and needle seat 332) via port P22, thereby pressurizing the sample in the sample loop 320. The output of the sample loop 320 (e.g., a mixture of the first solvent and the sample) is connected to port P25, which is connected to port P26 via groove G23 of the second valve 312. The output of port P26 is connected to port P15 of the first valve 311, which is connected to plugged port P24 via groove G13, as described above. Once the sample loop 320 is pressurized to the pressure provided by booster pump 103, relying in large part on the influx of the pressurized first solvent, there will not be any flow through the sample loop 320. In this manner, the mobile phase from the mobile phase pumping system 110 remains in direct communication to separation unit 130, without interruption or other disturbance, while the sample loop 320 is being pressurized.

Notably, in above description, the second valve 312 is switched by rotating the rotor counter-clockwise with respect to the stator. However, this direction of movement is merely for purposes of illustration, and it is understood that the same practical configuration may be obtained by rotating the rotor of the second valve 312 clockwise. In this case, ports P21 and P22 would be joined by groove G22, ports P23 and P24 would be joined by groove G23, and ports P25 and P26 would be joined by groove G21, without departing from the scope of the present teachings.

FIG. 3C depicts a subsequent configuration of the valve assembly 310 (third step) for delivering pressurized sample via the mobile phase to the separation unit 130. In particular, FIG. 3C shows placement of the sample loop 320 containing the pressurized sample into the mobile phase, thereby injecting the sample into the separation unit 130.

More particularly, the first valve 311 is configured (or switched) such that ports P11 and P12 are joined by groove G11, ports P13 and P14 are joined by groove G12, and ports P15 and P16 are joined by groove G13. In this configuration, the mobile phase entering the first valve 311 is diverted through the second valve 312 in order to place the sample loop 320 containing the pressurized sample into the mobile phase, without interrupting flow of the mobile phase (still from port 16) into the separation unit 130. That is, the mobile phase is received from the mobile phase pumping system 110 at port P11 and exits port P12 to the port 21 of the second valve 312. The mobile phase exits port P22 and enters the sample loop 320, thereby placing the pressurized sample loop 320 (and pressurized first solvent filling lines) into the combined solvent of the mobile phase. The output of the sample loop 320, now including the mobile phase containing the sample, enters port P25 and exits port P26, which is connected to port P15 of the first valve 311. The sample containing mobile phase enters port P15 and exits port P16, and is directed to the separation unit 130. Meanwhile, the sample provided by the autosampler metering device 333 continues to be received by port P23, and exits port P24 of the second valve 312 to waste. In this manner, the sample loop 320 is switched into the mobile phase, thereby introducing the pressurized sample to the separation unit 130.

Again, in above description, the first valve 311 is switched by rotating the rotor counter-clockwise with respect tot the stator. However, this direction of movement is merely for purposes of illustration, and it is understood that the same practical configuration may be obtained by rotating the rotor of the first valve 311 clockwise. In this case, ports P11 and P12 would be joined by groove G12, ports P13 and P14 would be joined by groove G13, and ports P15 and P16 would be joined by groove G11, without departing from the scope of the present teachings.

Throughout the various steps and corresponding configurations of the valve assembly 310 discussed above with reference to FIGS. 3A-3C, the mobile phase from the mobile phase pumping system 110 remains in direct communication to separation unit 130, without interruption or other disturbance, while the sample loop 320 is being pressurized. Also, the pressurized sample is introduced into the mobile phase without interrupting delivery of the mobile phase to the separation unit 130. In other words, with all lines leading to and from the sample loop 320 being pressurized, flow of the mobile phase is not interrupted and diverted (temporarily) for pressurization, as in conventional chromatographic systems.

Thus, the efficiency of loading sample (already under pressure) into the mobile phase is significantly improved, in both embodiments, shown in FIGS. 2A-2C and FIGS. 3A-3C, respectively. Although not shown in FIGS. 2A-2C or in FIGS. 3A-3C, it is understood that other types and combinations of numbers and types of valves may be incorporated within the valve assemblies 210, 310, without departing from the scope of the present teachings. For example, the use of two position, ten port switching valves, or other combinations of switching, rotary selection, solenoid, or other valving techniques may be adaptively substituted to perform the same operations. So long as the sample loop is pressurized with pressurized first solvent and switched into the mobile phase stream prior to separation, without interrupting flow of the mobile phase stream or otherwise depressurizing the mobile phase pumping system while the sample loop is being pressurized, mobile phase interruption and other disruption is avoided.

Figure 4:
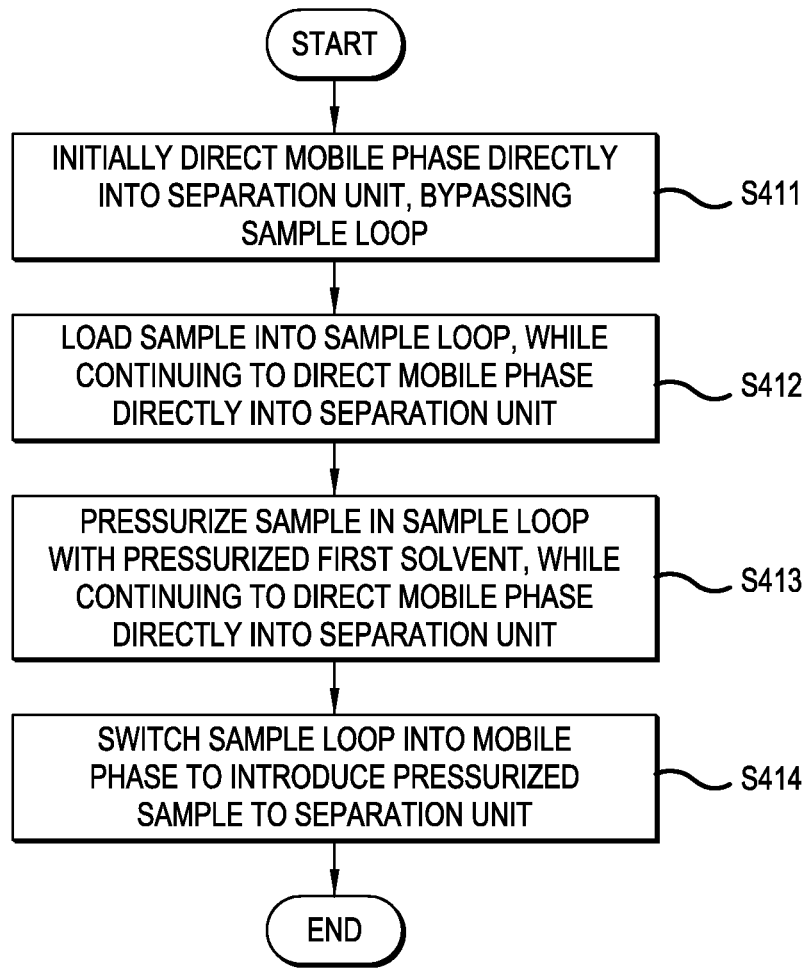
FIG. 4 is a flow diagram illustrating a method of introducing a sample into a mobile phase of a chromatography system without disrupting flow of the mobile phase into the column, according to a representative embodiment.

FIG. 4 is a flow diagram illustrating a method of introducing a sample into a mobile phase of a chromatography system, according to a representative embodiment.

Referring to FIG. 4, the mobile phase is initially directed from a mobile phase delivery apparatus (e.g., mobile phase delivery apparatus 110) directly into a separation unit (e.g., separation unit 130) of the chromatography system in block S411, bypassing a sample loop (e.g., sample loop 220, 320). The mobile phase includes a combined solvent, metered from a first solvent and a second solvent. The first solvent may be pressurized (e.g., by booster pump 103) prior to metering by the mobile phase delivery apparatus. As discussed above, the first solvent may be a weak solvent (e.g., carbon dioxide $CO_2$) and the second solvent may be a strong solvent (e.g., methanol).

In block S412, the sample is loaded into the sample loop, while the mobile phase continues to be directed directly via a sample introducing apparatus (e.g., sample introducing apparatus 120) into the separation unit. The step of sample loading, block s412, implicitly contains any required SPE related operations (e.g. solvent removal). The sample is pressurized in the sample loop in block S413 using the pressurized first solvent, while the mobile phase continues to be directed directly into the separation unit. Also, the mobile phase from the mobile phase pumping system 110 remains pressurized while the sample loop is being pressurized. In block S414, the sample loop with the pressurized sample is switched into the mobile phase, thereby introducing the pressurized sample to the separation unit without interruption of flow of the mobile phase. Also, the sample is pressurized in the sample loop in block S413 without disturbing the metering of the combined solvent by the mobile phase delivery apparatus.

In an embodiment, the pressurized first solvent may be provided by a booster pump pumping the first solvent from a first reservoir (e.g., first reservoir 101), which may be a pressurized tank of $CO_2$, for example. In this case, the combined solvent may include the pressurized first solvent from the booster pump and the second solvent is provided by a second reservoir (e.g., second reservoir 102) both metered by mobile phase pumping system 110 for delivery to separation unit 130.

In various embodiments, the sample loop may include or be comprised by a retentive device, column, or SPE cartridge, for example, for separating analytes of the sample from the sample solvent (e.g., methanol, water, or other solvent incompatible in strength or miscibility, for example, with the mobile phase) prior to entry of the mobile phase into SPE cartridge. The mobile phase carries the analytes of the sample, essentially devoid of initial sample solvent to the separation device, which separates the analytes of the sample using the partitioning between the stationary phase of the separation device and the mobile phase for analysis. Thus, generally speaking, loading the sample into the sample loop (e.g., SPE cartridge) may include initially removing at least some sample solvent of the sample within the sample loop, while retaining at least some sample analytes of the sample within the sample loop.

One of ordinary skill in the art appreciates that many variations that are in accordance with the present teachings are possible and remain within the scope of the appended claims. These and other variations would become clear to one of ordinary skill in the art after inspection of the specification, drawings and claims herein. The invention therefore is not to be restricted except within the spirit and scope of the appended claims.

What is claimed:

1. A system for introducing a sample into a mobile phase directed to a separation unit of a chromatography system, the system comprising:
   a mobile phase pumping system configured to meter a combined solvent as the mobile phase, the mobile phase comprising a strong solvent and a weak solvent, and pressurize the mobile phase, the mobile phase pumping system further configured to direct a flow of the pressurized mobile phase to the separation unit;
   a booster pump configured to pressurize the weak solvent and deliver a first portion of a flow of the pressurized weak solvent to the mobile phase pumping system and a second portion of the flow of the pressurized weak solvent to a sample loop; and
   a valve assembly disposed upstream from the separation unit and configured to pressurize the sample loop loaded with the sample using the second portion of the flow of the pressurized weak solvent, the second portion supplied to the valve assembly being pressurized by the booster pump, and subsequently to switch the pressurized sample loop into the pressurized mobile phase, thereby introducing the pressurized sample into the pressurized mobile phase prior to introduction of the pressurized sample into the separation unit;
   wherein the mobile phase from the mobile phase pumping system remains pressurized while the sample loop is being pressurized by the booster pump.

2. The system of claim 1, wherein the pressurized sample is introduced into the mobile phase without interrupting delivery of the mobile phase to the separation unit.

3. The system of claim 1, further comprising:
   means for controlling loading of the sample into the sample loop.

4. The system of claim 3, wherein the means for controlling loading of the sample into the sample loop comprises an autosampler including a needle for insertion into a vial containing the sample, a needle seat for interfacing the needle with the sample loop, and a metering device for drawing the sample from the vial via the needle.

5. The system of claim 3, wherein the sample loop comprises a retentive device, column, or solid phase extraction (SPE) cartridge.

6. The system of claim 5, wherein the means for controlling loading into the sample loop comprises an SPE interface configured to remove at least some sample solvent of the sample from the sample loop.

7. The system of claim 1, wherein the separation unit comprises a chromatographic column comprising a stationary phase.

8. The system of claim 7, wherein the weak solvent comprises carbon dioxide, and the strong solvent comprises methanol or other organic solvent.

9. The system of claim 1, wherein the sample loop comprises a needle and a needle seat for the needle, the needle being configured for insertion into a vial of the sample to enable loading of the sample loop with the sample.

10. A system for introducing a sample into a mobile phase directed to a separation unit of a chromatography system, the system comprising:
    a booster pump configured to pressurize a solvent and to deliver a first portion of the pressurized solvent to a mobile phase pumping system and a second portion of the pressurized solvent to a sample loop;
    the mobile phase pumping system being configured to meter the first portion of the pressurized solvent supplied from the booster pump as at least a portion of the mobile phase, to pressurize the mobile phase, and to direct a flow of the pressurized mobile phase to the separation unit;
    a valve assembly disposed upstream of the separation unit and configured to pressurize a sample loop loaded with the sample using the second portion of the pressurized solvent, the second portion supplied to the valve assembly being pressurized by the booster pump, and to subsequently introduce the pressurized sample into the pressurized mobile phase, thereby pressurizing the sample prior to introduction into the pressurized mobile phase;
    wherein the mobile phase from the mobile phase pumping system remains pressurized while the sample loop is being pressurized by the booster pump.

11. The system of claim 10, wherein a pressure of the solvent pressurized by the booster pump is controlled to be below an output pressure of the mobile phase pumping system.

* * * * *